US 9,707,355 B2

(12) United States Patent
Döker et al.

(10) Patent No.: US 9,707,355 B2
(45) Date of Patent: Jul. 18, 2017

(54) METHOD FOR COATING ELONGATE OBJECTS

(71) Applicant: Nordson Corporation, Westlake, OH (US)

(72) Inventors: Andreas Döker, Fürstenfeldbruck (DE); Thomas Wanka, Kaufbeuren (DE); Michael Wilczek, Germering (DE)

(73) Assignee: NORDSON CORPORATION, Westlake, OH (US)

( * ) Notice: Subject to any disclaimer, the term of this patent is extended or adjusted under 35 U.S.C. 154(b) by 89 days.

(21) Appl. No.: 14/279,927

(22) Filed: May 16, 2014

(65) Prior Publication Data

US 2014/0248419 A1   Sep. 4, 2014

Related U.S. Application Data

(62) Division of application No. 13/114,300, filed on May 24, 2011, now Pat. No. 8,757,087.

(51) Int. Cl.
| *A61M 5/32* | (2006.01) |
| *B05B 7/04* | (2006.01) |
| *B05B 7/10* | (2006.01) |
| *B05B 7/00* | (2006.01) |
| *B05B 7/12* | (2006.01) |
| *B05D 1/02* | (2006.01) |
| *B05D 5/08* | (2006.01) |
| B05B 13/02 | (2006.01) |

(52) U.S. Cl.
CPC .............. *A61M 5/32* (2013.01); *A61M 5/329* (2013.01); *B05B 7/0012* (2013.01); *B05B 7/045* (2013.01); *B05B 7/10* (2013.01); *B05B 7/12* (2013.01); *B05B 13/0214* (2013.01); *B05D 1/02* (2013.01); *B05D 5/08* (2013.01); *A61M 2205/0222* (2013.01); *A61M 2205/0238* (2013.01); *A61M 2207/10* (2013.01); *B05B 13/0207* (2013.01)

(58) Field of Classification Search
CPC .................................. B05D 5/12; B05B 13/06
USPC .......................... 427/131, 127, 162; 118/317
See application file for complete search history.

(56) References Cited

U.S. PATENT DOCUMENTS

| 4,106,519 | A | 8/1978 | Jalil et al. |
| 4,221,339 | A | 9/1980 | Yoshikawa |
| 5,186,972 | A | 2/1993 | Williams et al. |
| 5,258,013 | A | 11/1993 | Granger et al. |
| 5,266,359 | A | 11/1993 | Spielvogel |

(Continued)

FOREIGN PATENT DOCUMENTS

| DE | 2213984 A1 | 10/1973 |
| WO | 0043570 A1 | 7/2000 |

OTHER PUBLICATIONS

EP Application No. 12 16 9382, Partial European Search Report dated Mar. 27, 2014, 7 pages.

(Continued)

*Primary Examiner* — Dah-Wei D Yuan
*Assistant Examiner* — Andrew Bowman
(74) *Attorney, Agent, or Firm* — Baker & Hostetler LLP

(57) ABSTRACT

A method of coating an exterior surface of the elongate object with the coating material includes holding the elongate object lengthwise in the elongate chamber, mixing the pressurized air and the coating material to form a mist, and coating the exterior surface while directing the mist around the exterior surface and toward the outlet of the elongate chamber.

10 Claims, 4 Drawing Sheets

(56) References Cited

U.S. PATENT DOCUMENTS

| | | |
|---|---|---|
| 5,529,055 A | 6/1996 | Gueret |
| 5,536,582 A | 7/1996 | Prasad et al. |
| 5,628,826 A | 5/1997 | Prasad |
| 5,653,695 A | 8/1997 | Hopkins et al. |
| 5,743,963 A | 4/1998 | Williamitis et al. |
| 5,911,711 A | 6/1999 | Pelkey |
| 6,117,480 A | 9/2000 | Spallek et al. |
| 6,312,759 B1 * | 11/2001 | Yamada ............... C07C 17/23 134/42 |
| 6,368,658 B1 | 4/2002 | Schwarz et al. |
| 6,540,831 B1 | 4/2003 | Craine et al. |
| 6,656,167 B2 | 12/2003 | Numao et al. |
| 6,811,136 B2 | 11/2004 | Eberhardt et al. |
| 6,811,805 B2 | 11/2004 | Gilliard et al. |
| 6,890,345 B2 | 5/2005 | Roby et al. |
| 6,979,473 B2 | 12/2005 | O'Connor et al. |
| 7,008,979 B2 | 3/2006 | Schottman et al. |
| 7,041,088 B2 | 5/2006 | Nawrocki et al. |
| 7,335,264 B2 * | 2/2008 | Motherwell ......... B05B 7/0416 118/306 |
| 7,338,557 B1 | 3/2008 | Chen et al. |
| 7,354,628 B2 | 4/2008 | Steube |
| 7,604,699 B2 | 10/2009 | Chen et al. |
| 8,409,656 B2 | 4/2013 | Bay et al. |
| 9,221,075 B2 | 12/2015 | Maurer et al. |
| 2003/0064152 A1 | 4/2003 | Takimoto et al. |
| 2005/0203201 A1 | 9/2005 | Steube |
| 2007/0145164 A1 | 6/2007 | Ahmadi et al. |
| 2007/0254091 A1 | 11/2007 | Fredrickson et al. |
| 2007/0289492 A1 | 12/2007 | Wynne et al. |
| 2007/0299409 A1 | 12/2007 | Whitbourne et al. |
| 2008/0065155 A1 | 3/2008 | Waeschle |
| 2008/0131585 A1 | 6/2008 | Chen et al. |
| 2008/0216704 A1 | 9/2008 | Eisenbeis et al. |
| 2009/0024097 A1 | 1/2009 | Okoniewski |
| 2009/0048537 A1 | 2/2009 | Lydon et al. |
| 2009/0138077 A1 | 5/2009 | Weber et al. |
| 2009/0162530 A1 | 6/2009 | Nesbitt |
| 2009/0255260 A1 | 10/2009 | McMasters et al. |
| 2009/0318746 A1 | 12/2009 | Thurmond, II et al. |
| 2010/0015333 A1 | 1/2010 | McMorrow |
| 2010/0023053 A1 | 1/2010 | Akutsu et al. |
| 2010/0030109 A1 | 2/2010 | Lin |

OTHER PUBLICATIONS

EP Application No. 12 16 9382, Extended European Search Report dated Sep. 1, 2015, 8 pages.
European Application No. 16159480.9: European extended Search Report dated Sep. 16, 2016.

* cited by examiner

METHOD FOR COATING ELONGATE OBJECTS

CROSS-REFERENCE TO RELATED APPLICATION

This application is a divisional of U.S. application Ser. No. 13/114,300, filed May 24, 2011 (pending), the disclosure of which is incorporated by reference herein.

TECHNICAL FIELD

The present invention generally relates to the application of coatings onto exterior surfaces of objects and, more specifically, the coating of elongate objects such as needles.

BACKGROUND

Elongate objects are coated with material for various reasons. For example, hypodermic needles are often coated with lubricious or friction-reducing materials, such as silicone based oils. This provides a low friction outer surface of the needle for purposes of easing the introduction of the needle through the skin of a patient. Various methods and apparatus for applying the coating material to the needle have been used in the past. These include dipping methods in which the needles are dipped lengthwise into a bath containing silicone and solvent. This method presents difficulties and challenges related to handling the silicone and solvents, as well as the lengthy drying times involved, and the ventilation needs due to the use of the solvents.

Other methods that have been employed in the past involve various manners of spraying the coating material onto the needle. Typically, the spraying device will discharge the coating material in a single direction and the material will not flow around the entire exterior of the needle. For this reason, the needle and/or spray dispenser must be rotated to evenly distribute the coating material on the entire exterior surface of the needle. Alternatively, multiple spraying devices may be used to coat all sides of the needle. Either case involves increased complication and expense. The overspray or mist can also present problems in the environment around the equipment or require apparatus for containing the overspray. Due to the viscosity of the fluid coating material, it can also be difficult to achieve the required thin, uniform layer of coating material on the exterior surface of the needle.

It would therefore be desirable to provide a device and method for easily coating an exterior of an elongate workpiece, such as a needle, while addressing various challenges presented by past devices and methods.

SUMMARY

The present invention generally provides a device for coating an exterior of an elongate object. The device generally comprises a housing structure including an elongate coating chamber having first and second opposite ends. A port communicates with the first end for receiving the elongate object into the coating chamber and an outlet at the second end. The coating chamber has at least first and second sections. The first section is located closer to the outlet than the second section and the first section has a greater cross sectional area than the second section. The housing structure further includes an air supply passage and a coating material supply passage communicating with the elongate coating chamber. The pressurized air and coating material are adapted to enter the elongate chamber through the air supply passage and the coating material supply passage, respectively, to form a mist of the air and coating material. This mist is directed into the elongate chamber and generally toward the outlet while coating the exterior of the elongate object inserted into the elongate chamber through the port.

In a more specific embodiment, a mixing passage communicates with the air supply passage and the coating material supply passage. The mixing passage further communicates with the elongate chamber. The pressurized air and the coating material enter the mixing passage through the air supply passage and the coating material supply passage, respectively, and the mist of the air and coating material begins to form in the mixing passage before entering the elongate chamber.

A device constructed according to the exemplary embodiment further includes various additional features. For example, a valve comprised of a valve member and a valve seat selectively supplies the coating material to the elongate chamber. A ring shaped structure communicates between the air supply passage and the mixing passage. The ring shaped structure is configured to cause the pressurized air to enter the mixing passage with a swirling motion about a discharge location of the coating material into the mixing passage. The ring shaped further includes a central passage through which the coating material is directed into the mixing passage and into the air moving with the swirling motion. The device may further include a coating material injecting element including a tube with an outlet. The tube extends through the central passage with the outlet of the tube positioned in the mixing passage. The ring shaped structure more specifically includes a ring shaped wall surrounding an inner space and disposed around a central axis. The central passage extends along the central axis. The ring shaped wall further includes a plurality of air directing passages communicating between the air supply passage and the inner space so as to achieve the swirling motion around the central axis. The ring shaped structure further comprises a plurality of stand-off elements forming additional air passages between the stand-off elements and providing communication between the air supply passage and the mixing passage.

The elongate chamber is preferably configured with increasing diameter in a direction from the first end to the second end so that an increase in pressure is achieved in this direction within the chamber. The flow of the mist is generally along a central axis of the elongate chamber coaxial with the port at the first end. The mixing passage extends transverse, and more preferably perpendicular, to the elongate chamber.

The elongate object further comprises a hollow needle having opposite, open ends, such as a hypodermic syringe needle. The device further comprises a needle holder including an interior air space and a needle holding element configured to secure a first end of the needle in communication with the interior air space. The open second end of the needle extends outwardly from the needle holder for insertion through the port and into the elongate chamber. The interior air space is adapted to be pressurized with air to force air through the needle during a coating operation and prevent clogging of the open second end of the needle with the coating material.

In another aspect, a method is provided for coating an exterior surface of an elongate object with a coating material. The method generally includes holding the elongate object lengthwise in an elongate chamber having first and second opposite ends and an outlet at the second end. A mist is formed from a mixture of the air and the coating material and the exterior surface is coated with the coating material while directing the mist around the exterior surface of the elongate object and toward the outlet of the elongate chamber.

The method practiced according to an illustrative example includes various additional aspects and steps. For example, the pressurized air and the coating material are first mixed within a mixing passage oriented transverse to the elongate chamber prior to directing the air and the coating material into the elongate chamber as a mist. The mixing passage extends along an axis and the method further comprises swirling the air around the axis of the mixing passage at an air inlet to the mixing passage, and directing the coating material into the mixing passage along the central axis to mix with the swirling air. The method further comprises directing the air into the mixing passage with a Venturi effect. Holding the elongate object further comprises directing the object through a port at the first end of the elongate chamber and the method further comprises directing additional air through the port and adjacent the object toward the outlet of the elongate chamber. The elongate object further comprises a hollow needle with opposite, first and second open ends, and the method further comprises directing air through the first open end of the needle and out of the second open end positioned in the elongate chamber to prevent clogging of the first open end with the coating material. Directing the coating material into the elongate chamber further comprises actuating a valve to allow pressurized coating material to flow into the elongate chamber. The coating material may be a friction reducing material, such as a material containing silicone.

Various additional features and advantages of the invention will become more apparent to those of ordinary skill in the art upon review of the following detailed description of the illustrative embodiments taken in conjunction with the accompanying drawings.

DETAILED DESCRIPTION OF THE ILLUSTRATIVE EMBODIMENTS

Figure 1:
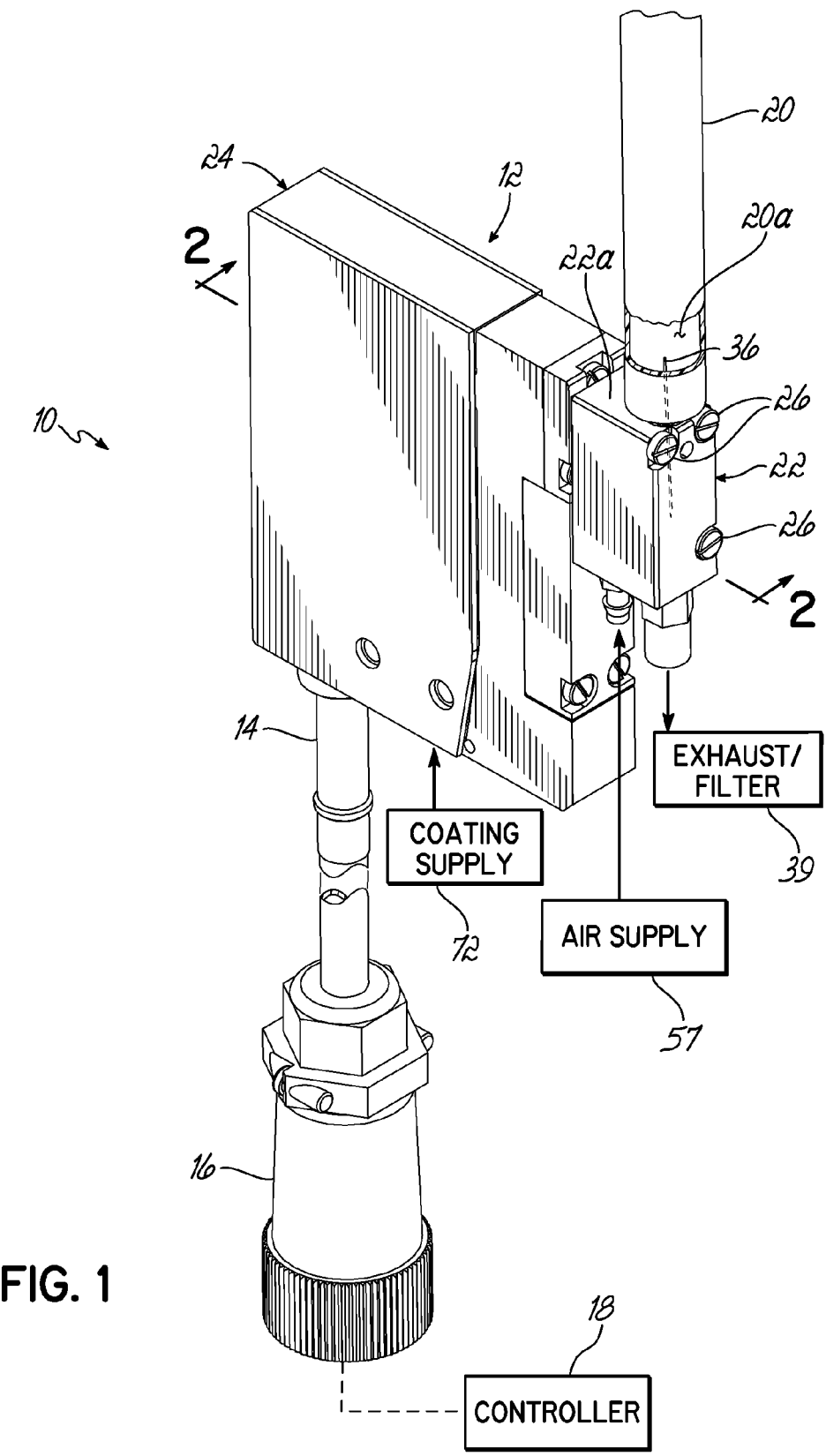
FIG. 1 is a perspective view of a device constructed in accordance with an illustrative embodiment of the invention.

FIG. 1 illustrates a device 10 generally comprising a housing structure 12 coupled with a conduit 14 suitable for containing control and electrical supply wiring (not shown). An electrical coupler 16 is provided and adapted to couple the device 10 to a controller 18 for operating the device 10. A needle holder 20 is provided for introducing a needle to be coated, as further discussed below, into the housing structure 12. More specifically, the needle holder 20 is adapted to abut an outside face 22a of a first sub-housing 22 coupled to a second sub-housing 24 of the housing structure 12 by fasteners 26.

Figure 2:
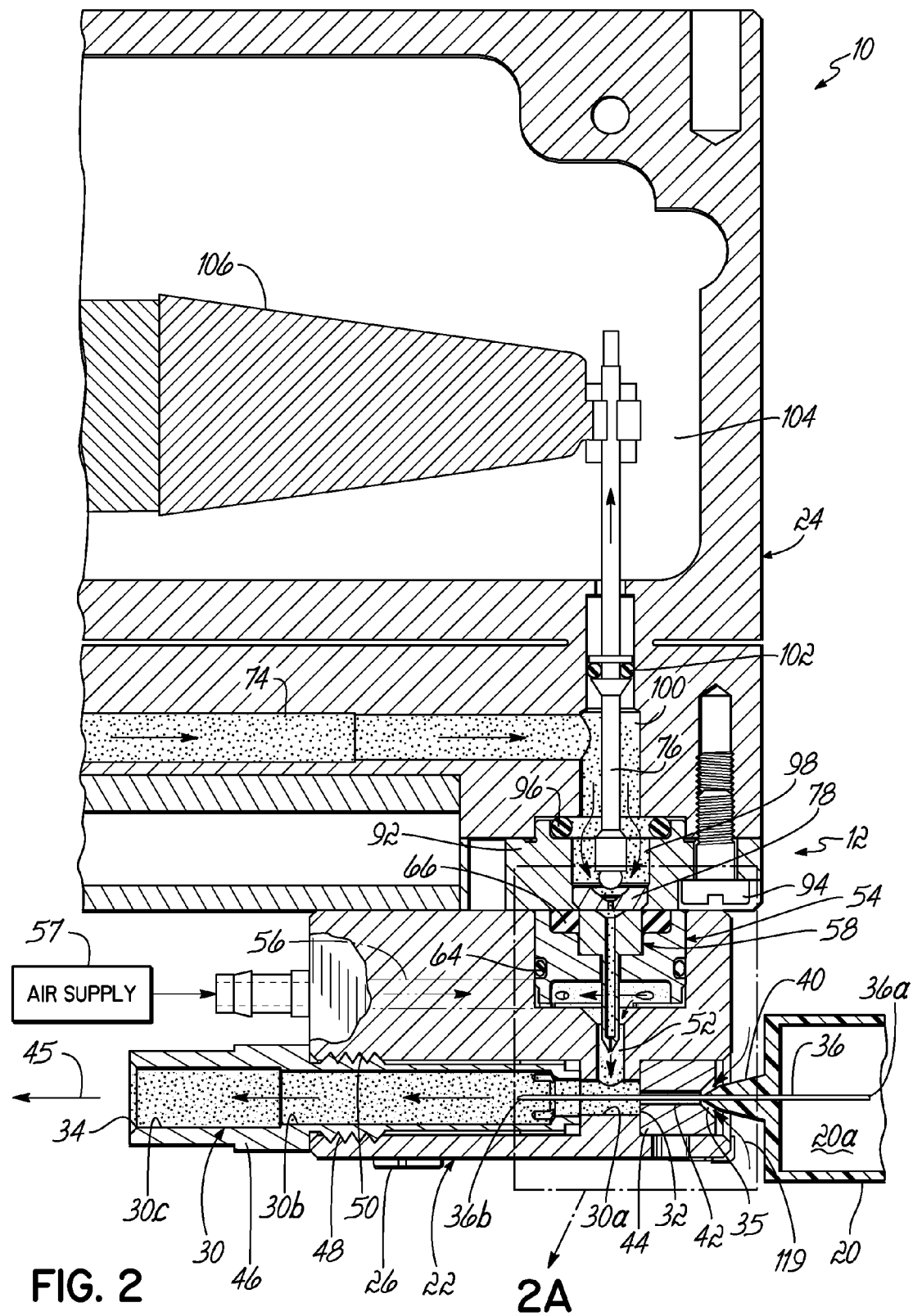
FIG. 2 is a cross sectional view generally taken along line 2-2 of FIG. 1 and rotated 90° for purposes of easier explanation.
Figure 2A:
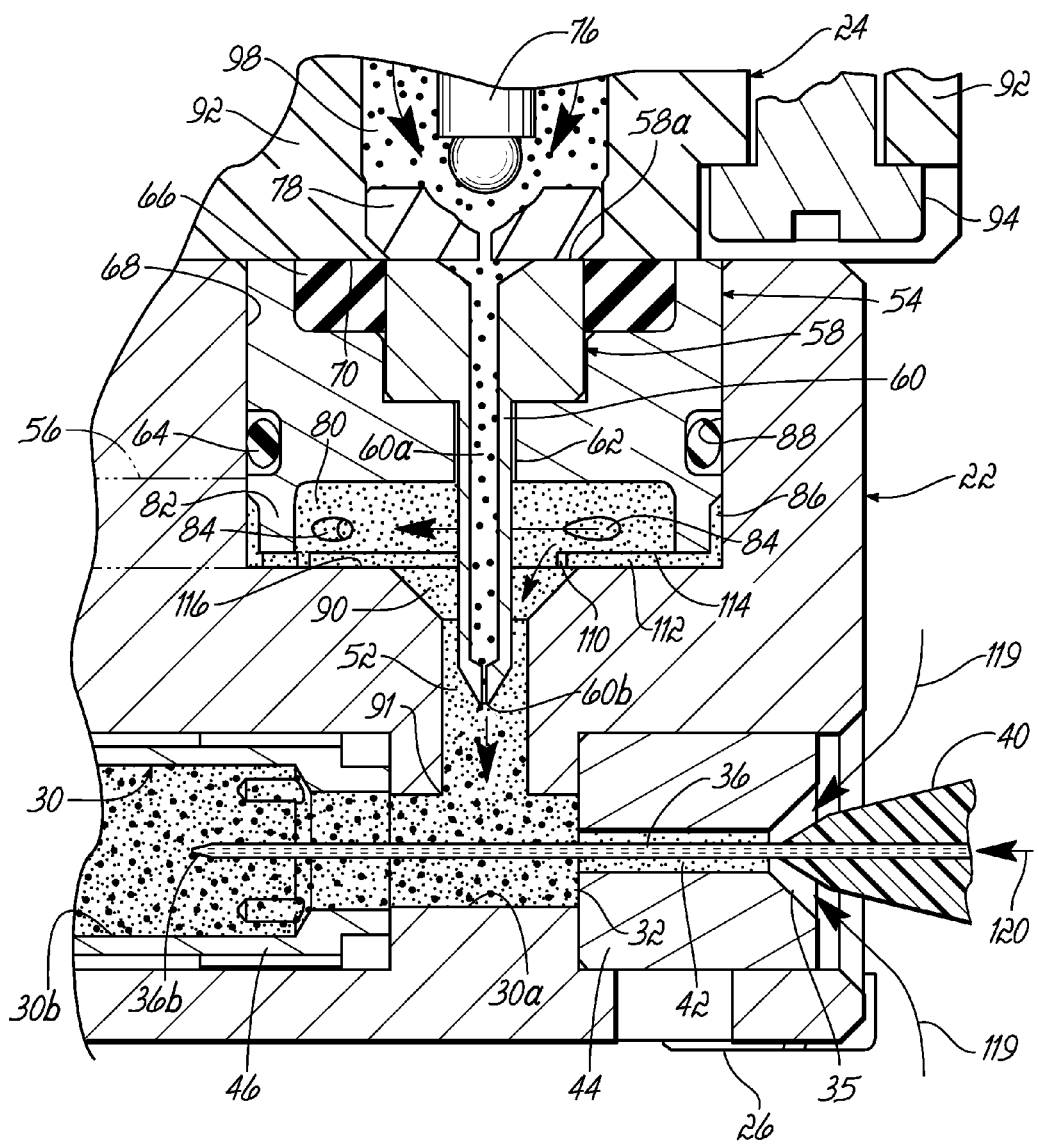
FIG. 2A is an enlarged view of the portion marked "2A" in FIG. 2.

Referring to FIGS. 2 and 2A, the first sub-housing 22 more specifically comprises an elongate chamber 30 having first and second opposite ends 32, 34. A port 35 at the first end 32 receives a needle 36 for coating purposes. The second end 34 defines an outlet. As shown in FIG. 1, the second end is fluidly coupled to an exhaust 39 including a filter. The needle holder 20 is mounted for movement in a manner (not shown) that allows for repeatable introduction of successive needles 36 into the chamber 30 during a manufacturing operation. The needle holder 20 includes an interior air space 20a and a needle holding element 40. The needle holding element 40 grips the needle 36 with friction or in any other suitable manner such that an open first end 36a communicates with the interior air space 20a and an open second end 36b is positionable within the elongate chamber 30. The needle 36 extends through the port 35 preferably along the central axis of the port 35 and the elongate chamber 30. The needle 36 extends through a passage 42 in an insert 44 within the first sub-housing 22 and the port 35 more specifically comprises a conically shaped opening in the insert 44. As will be more specifically described below, air is drawn in through the conically shaped port 35 into the passage 42 of the insert 44 and, finally, into the elongate chamber 30. The elongate chamber 30 comprises cylindrical chamber portions 30a, 30b, 30c of successively larger diameter for creating an increasing pressure as pressurized air flows from the first end 32 toward the second end 34 in the direction of the arrows 45. At least a portion of the elongate chamber 30 may be formed by the interior of a tubular member 46 that is removably attached to the first sub-housing 22 by respective threads 48, 50.

A mixing passage 52 in the first sub-housing 22 extends transverse and, more specifically, perpendicular to the elongate chamber 30. This mixing passage 52 communicates directly with the smallest diameter chamber portion 30a adjacent the insert 44 and needle port 35. As best shown in FIG. 2A, the first sub-housing 22 further includes a ring shaped structure 54 for receiving pressurized air from an air supply passage 56. The air supply passage 56 is coupled with a source 57 of pressurized air. The pressure of the air is preferably in the range of one to four bar. The ring shaped structure 54 further receives a coating material injecting element 58 including a tube 60 with a passage 60a and an outlet 60b extending through a central passage 62 of the ring shaped structure 54. The ring shaped structure 54 more specifically comprises a ring sealed by respective O-rings 64, 66 within a recess 68 of the first sub-housing 22 and against a surface 70 of the second sub-housing 24.

Figure 3:
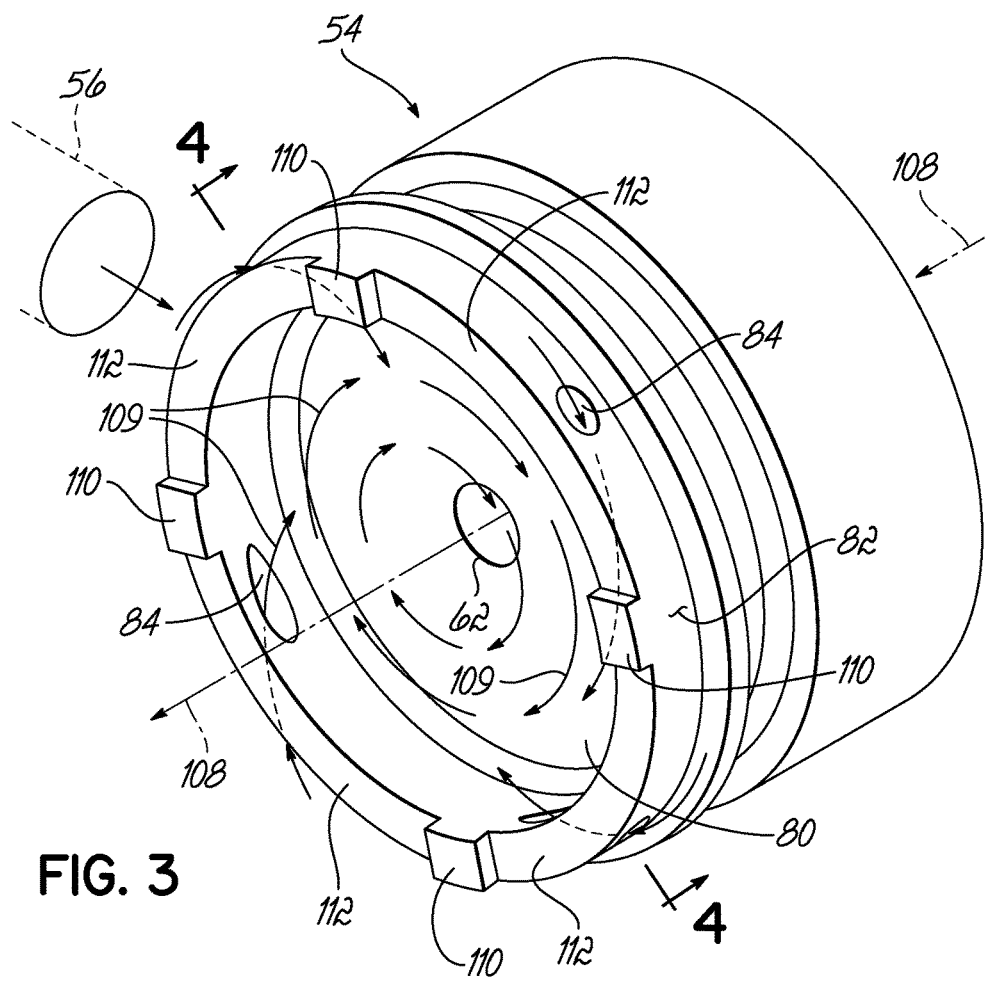
FIG. 3 is a perspective view of the ring shaped structure used to direct the air flow within the device of FIG. 1.
Figure 4:
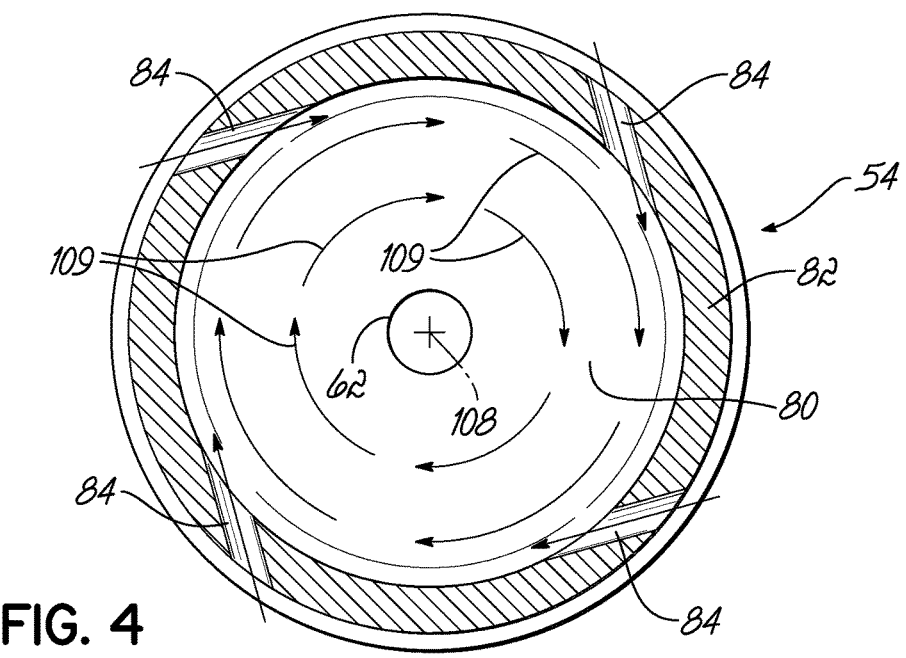
FIG. 4 is a cross sectional view taken generally along line 4-4 of FIG. 3.

The coating material is provided from a suitable pressurized supply 72 (FIG. 1). In the case of coating a hypodermic syringe needle, for example, the coating materials are preferably silicone oils of various viscosity ranging, for example, from the viscosity of water to 12,500 mPas. Most applications currently contemplated will utilize a viscosity of 1000-3000 mPas. The coating material is directed through a supply passage 74 (FIG. 2) and ultimately into the central passage 60a of the tube 60 and is injected into the mixing passage 52 when a valve element 76 positioned in the second sub-housing 24 is opened relative to a valve seat element 78 abutting an inlet end 58a of the coating material injecting element 58. As will be described further in connection with FIGS. 3 and 4, the ring shaped structure 54 receives and directs the air in a swirling motion within an inner space 80 defined by a ring shaped or annular wall 82. The ring shaped wall 82 includes a plurality of air directing passages 84 communicating with the air supply passage 56 through an annular air space 86 formed between the ring shaped wall 82 and the wall 88 of the recess 68. The swirling air within an inner space 80 is directed downwardly into a generally cone-shaped or converging passage 90 surrounding the tube 60 of the coating material injecting element 58 and then into the mixing passage 52. Due to the constriction formed by the converging passage 90, the air is directed into the mixing passage with a Venturi effect in addition to the swirling motion. The air then mixes with the injected coating material to form a mixture in the form of a mist as the air and coating material enter the elongate chamber 30 through a connecting port 91.

More specifically referring to FIG. 2, the valve seat element 78 is carried on a valve component 92 affixed to a main part of the second sub-housing 24 by threaded fasteners 94 (only one shown). The valve component 92 is mounted in sealing engagement with the main part of the second sub-housing 24 through the use of an 0-ring 96. A passage 98 of the valve component 92 communicates with a passage 100 in the second sub-housing 24 containing the reciprocating valve element or valve stem 76. The passage 100 communicates with the coating material supply passage 74 and, ultimately, with the coating material supply 72 (FIG. 1). The valve stem 76 includes an additional dynamic seal 102 engaged with the internal wall defining the passage 100 to prevent the coating material from leaking into the interior space 104 of the second sub-housing 24 which contains valve stem actuating components, including an actuating arm 106. The valve stem 76 and actuating arm 106 may be actuated in any suitable manner such as by using a conventional piezo-electric actuator (not shown).

Referring to FIG. 2A in combination with FIGS. 3 and 4, the ring shaped structure 54 includes the ring shaped wall 82 surrounding the inner space 80 and the wall 82 is spaced around a central axis 108. The central passage 62 extends in a coaxial fashion around the central axis 108 and the ring shaped wall 82 further includes the plurality of air directing passages 84 communicating with the annular space 86 (FIG. 2A) which, in turn, communicates with the pressurized air supply passage 56. The air directing passages 84 are formed in a generally tangential manner relative to the cylindrical shape of the inner space 80 as best illustrated in FIG. 4 such that air entering the inner space 80 travels with a swirling motion as shown by the arrows 109. A plurality of stand-off elements 110 extends from a lower end of the ring shaped structure 54 and provide for additional air passages or paths 112 (FIG. 2A) between the stand-off elements 110 and between lower surfaces 114 of the ring shaped structure 54 and the bottom wall 116 (FIG. 2A) of the recess 68, as shown in FIG. 2A. Therefore, air will enter an annular space 86 from the air supply passage 56 and, from the annular space 86, pass through the air directing passages 84 into the inner space 80, and also pass between the stand-off elements 110 through passages 112. The air passing through the air directing passages 84 will cause a swirling air motion within the inner space 80 and this air will be directed downwardly to combine with the air passing between the stand-off elements 110 and then enter the inlet 90 of the air mixing passage 52 with a swirling motion and Venturi effect, i.e., reduced pressure and increased velocity. This mixing action will begin to form a mist with the coating material being injected through the outlet 60*b* of the tube 60 along the central axis 108 of the ring shaped structure 54 and the coaxial central axis of the mixing passage 52. The flow within the elongate chamber 30 will draw additional air into the port 35 as shown by arrows 119 and through the passage 42 of the insert 44 (see FIGS. 2 and 2A) to prevent any coating material from traveling in the opposite direction through the port 35. At the same time, pressurized air in the interior air space 20*a* will travel as illustrated by the arrow 120 in FIG. 2A through the open first end 36*a* of the needle 36 and out of the open second end 36*b* of the needle 36 to prevent the second end 36*b* of the needle 36 from being clogged by coating material in the mist. The controller 18 (FIG. 1) will operate the actuating arm 106 to open and close the valve stem 76, and operate the pressurized air in an on/off fashion as necessary to successively coat multiple needles 36 in serial fashion as they are introduced one-by-one into the elongate chamber 30 by the same or different needle holders 20.

The first sub-housing 22 may be removed from the second sub-housing 24 for repair and replacement purposes. More specifically, components contained in the first sub-housing 22 may become contaminated due to the environmental air that is being suctioned into the passages of those components and mixed with the coating material. On the other hand, the components and passages associated with the second sub-housing 24 need much less service during regular use. Thus, the second sub-housing 24 and its associated components may remain mounted while the first sub-housing 22 and its attached components are removed from the second sub-housing by removing fasteners 26. The components 44, 46, 54, 58 associated with the first sub-housing 22 may be easily disassembled for cleaning purposes. In addition, the modular nature of the first sub-housing 22 allows different application requirements to be accommodated, such as size changes to accommodate different elongate objects, and adjustments to the type and/or viscosity of coating material. In addition, the injecting element 58 may be replaced to accommodate a coating material having a different viscosity. Finally, the insert 44 receiving the elongate object 36 may be modified for particular applications, such as coating operations of syringe tips with various configurations.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A method of coating an exterior surface of an elongate object with a coating material, the method comprising:

inserting the elongate object into a top of an elongate chamber having a bottom defining an outlet opposite the top;

directing pressurized air into a mixing passage through a plurality of air directing passages, the mixing passage having a first end and a second end spaced from the first end along a central axis, wherein the pressurized air is directed into the mixing passage in a central direction that extends parallel to the central axis of the mixing passage, and wherein the pressurized air swirls about the central axis of the mixing passage from the first end to the second end of the mixing passage;

directing the coating material into the mixing passage from the first end to the second end of the mixing passage, wherein the coating material is directed into the mixing passage in the central direction;

mixing the pressurized air and the coating material in the mixing passage to form a mist; and spraying the mist into the elongate chamber to coat the exterior surface of the elongate object with the coating material, the mist being directed around the exterior surface of the elongate object in the elongate chamber and toward the outlet of the elongate chamber.

2. The method of claim 1, further comprising:
directing the pressurized air into the mixing passage with a Venturi effect.

3. The method of claim 1, wherein inserting the elongate object further comprises directing the elongate object through a port communicating with the top of the elongate chamber, and the method further comprises:
directing additional air through the port and adjacent the elongate object toward the outlet of the elongate chamber.

4. The method of claim 1, wherein the elongate object further comprises a hollow needle with opposite, first and second open ends, and the method further comprises:
locating the second open end in the elongate chamber; and
directing air through the first open end of the hollow needle and out of the second open end to prevent clogging of the second open end with the coating material.

5. The method of claim 1, wherein directing the coating material further comprises:
actuating a valve to allow pressurized coating material to flow into the elongate chamber.

6. The method of claim 1, wherein the coating material comprises a friction reducing material.

7. The method of claim 1, wherein directing the mist toward the outlet further comprises:
directing the mist through sections of the elongate chamber having increasing diameter.

8. The method of claim 1, wherein the pressurized air swirls about the central axis at an inlet of the coating material into the mixing passage.

9. The method of claim 1, wherein the plurality of air directing passages are defined by a ring shaped structure.

10. The method of claim 1, wherein the coating material enters into the mixing passage through a tube.

\* \* \* \* \*